United States Patent
Cates et al.

(10) Patent No.: US 7,257,447 B2
(45) Date of Patent: Aug. 14, 2007

(54) METHOD AND APPARATUS FOR INDICATION-BASED PROGRAMMING OF CARDIAC RHYTHM MANAGEMENT DEVICES

(75) Inventors: Adam W. Cates, Minneapolis, MN (US); James O. Gilkerson, Stillwater, MN (US); Kenneth P. Hoyme, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 286 days.

(21) Appl. No.: 11/110,500

(22) Filed: Apr. 20, 2005

(65) Prior Publication Data
US 2006/0241712 A1   Oct. 26, 2006

(51) Int. Cl.
*A61N 1/362* (2006.01)
(52) U.S. Cl. .............................. 607/59; 607/31; 607/30; 607/60
(58) Field of Classification Search .................... 607/4, 607/5, 9, 30–32, 59, 60; 128/903, 904
See application file for complete search history.

(56) References Cited

U.S. PATENT DOCUMENTS

| | | | | |
|---|---|---|---|---|
| 5,292,341 A | * | 3/1994 | Snell | ............................ 607/30 |
| 5,360,437 A | * | 11/1994 | Thompson | .................... 607/30 |
| 5,716,382 A | | 2/1998 | Snell | |
| 5,722,999 A | | 3/1998 | Snell | |
| 5,817,137 A | | 10/1998 | Kaemmerer | |
| 6,110,108 A | | 8/2000 | Shimura et al. | |
| 6,168,563 B1 | | 1/2001 | Brown | |
| 6,358,203 B2 | | 3/2002 | Bardy | |
| 6,482,154 B1 | | 11/2002 | Haubrich et al. | |
| 6,522,925 B1 | | 2/2003 | Gilkerson et al. | |
| 6,648,823 B2 | | 11/2003 | Thompson et al. | |
| 6,690,972 B2 | | 2/2004 | Colney et al. | |
| 7,110,818 B2 | | 9/2006 | Anderson et al. | |
| 2002/0169488 A1 | | 11/2002 | Limousin et al. | |
| 2003/0171791 A1 | | 9/2003 | KenKnight et al. | |
| 2004/0181262 A1 | | 9/2004 | Bauhahn | |
| 2005/0043767 A1 | | 2/2005 | Belalcazar | |
| 2005/0245992 A1 | | 11/2005 | Persen et al. | |
| 2005/0256550 A1 | * | 11/2005 | Gilkerson et al. | ............ 607/60 |

FOREIGN PATENT DOCUMENTS

EP    1184050 A2    3/2002

OTHER PUBLICATIONS

"International Search Report and Written Opinion for Application No. PCT/US2006/014940, Dated Sep. 25, 2006", 10 Pages.
Kenknight, Bruce H., et al., "System and Method for Determining Patient-Specific Implantable Medical Device Programming Parameters", U.S. Appl. No. 10/950,876, filed Sep. 27, 2004 29 pgs.
Prystowsky, Eric N., "A Guide to Device Selection: Cardiac Resynchronization Therapy Alone or in Combination with an Implantable Cardioverter Defibrillator", *Pharmacomechanical Approach to CHF Treatmant, Reviews in Cardiovascular Medicine*, vol. 4, Suppl. 2, (2003), S47-S54.

* cited by examiner

*Primary Examiner*—Kennedy Schaetzle
(74) *Attorney, Agent, or Firm*—Schwegman, Lundberg, Woessner & Kluth, P.A.

(57) ABSTRACT

A cardiac rhythm management (CRM) system includes a programming device that determines parameters for programming an implantable medical device based on patient-specific information including indications for use of the implantable medical device. By executing an indication-based programming algorithm, the programming device substantially automates the process between the diagnosis of a patient and the programming of an implantable medical device using parameters individually determined for that patient.

36 Claims, 5 Drawing Sheets

METHOD AND APPARATUS FOR INDICATION-BASED PROGRAMMING OF CARDIAC RHYTHM MANAGEMENT DEVICES

CROSS-REFERENCE TO RELATED APPLICATIONS

This application is related to co-pending, commonly assigned, U.S. patent application Ser. No. 10/950,876, entitled "SYSTEM AND METHOD FOR DETERMINING PATIENT-SPECIFIC IMPLANTABLE MEDICAL DEVICE PROGRAMMING PARAMETERS," filed on Sep. 27, 2004 and U.S. patent application Ser. No. 10/844,642, entitled "METHOD AND APPARATUS FOR QUESTION-BASED PROGRAMMING OF CARDIAC RHYTHM MANAGEMENT DEVICES," filed on May 13, 2004, which are hereby incorporated by reference in their entirety.

FIELD OF THE INVENTION

This document generally relates to cardiac rhythm management (CRM) systems and particularly, but not by way of limitation, to a system for programming implantable CRM devices.

BACKGROUND

Implantable CRM devices such as pacemakers and defibrillators are used to treat cardiac arrhythmias, heart failure, and other cardiac disorders by delivering electrical energy to the heart. Advances in biomedical technology have provided implantable CRM devices with increasingly sophisticated features and operational modes treating more types of disorders while being more adaptive to a patient's changing physiological conditions and individual lifestyle. As a consequence, programming an implantable CRM device is an increasingly complicated task. To maximize the extent to which the patient can potentially benefit from the implantable CRM device, the programming needs to be substantially patient-specific.

To operate after implantation into a patient, an implantable CRM device is programmed by a physician or other caregiver using an external programming device. The programming device allows the physician or other caregiver to program the implantable CRM device by entering or selecting values for programmable parameters. Such programmable parameters include, but are not limited to, therapy modes and quantitative parameters required for operating in each therapy mode, special features and quantitative parameters required for utilizing each special feature, and various therapy activation or feature activation criteria. These parameters are determined by the physician or other caregiver for each patient based on the patient's indications for use of the implantable CRM device as well as other patient-specific data obtained during various diagnoses and tests. The increasing number of programmable parameters that accompany the increasingly sophisticated features and operational modes makes the parameter determination increasingly difficult. Additionally, implantable CRM devices of different types, as well as some devices of the same type, require different programmable parameters and/or different programming procedures. Physicians and/or other caregivers may have to receive extensive training on how to program each specific type of implantable CRM devices for an individual patient and how to optimally utilize many advanced features for the benefit of that patient. Introductions of new device features, while providing the users with additional power in treating cardiac disorders, tend to make the programming of implantable CRM devices more difficult and intimidating. One undesirable consequence is underutilization of available device features and capabilities. If properly utilized, such underutilized device features and capabilities will potentially provide substantial additional benefits to many patients who have already benefited from implantable CRM devices.

For these and other reasons, there is a need for facilitating the process of optimally programming an implantable CRM device for each individual patient.

SUMMARY

A CRM system includes a programming device that determines parameters for programming an implantable medical device based on patient-specific information including indications for use of the implantable medical device. By executing an indication-based programming algorithm, the programming device substantially automates the process between the diagnosis of a patient and the programming of an implantable medical device using parameters individually determined for that patient.

In one embodiment, an external system for programming an implantable medical device includes an external telemetry circuit and an indication-based programming device. The external telemetry circuit communicates with the implantable medical device. The indication-based programming device includes a patient information input, a device information input, an indication-based parameter generation module, and a programming module. The patient information input receives patient-specific information including indications for use of the implantable medical device. The device information input receives device-specific information including a device type indicative of a plurality of programmable parameters. The indication-based parameter generation module produces values for a set of operational parameters of the plurality of programmable parameters based on the patient-specific information and the device-specific information. The programming module programs the implantable medical device using the values of the set of operational parameters.

In a further embodiment, a cardiac rhythm management (CRM) system includes the external system and an implantable medical device. The implantable medical device is identified by a device type indicative of one or more available operational modes and a plurality of programmable parameters.

In one embodiment, a method for programming an implantable medical device is provided. Patient-specific information including indications for use of the implantable medical device is collected. Device-specific information including a device type of the implantable medical device is received. The device type indicates one or more available operational modes and a plurality of programmable parameters of the implantable medical device. An indication-based programming algorithm is executed to produce values for a set of operational parameters of the plurality of programmable parameters based on the patient-specific information and the device-specific information. A user election is received to determine whether to accept, modify, or discard the values for the set of operational parameters.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

In the drawings, which are for illustrative purposes only and not necessarily drawn to scale, like numerals describe similar components throughout the several views. The drawings illustrate generally, by way of example, various embodiments discussed in the present document.

DETAILED DESCRIPTION

Figure 1:
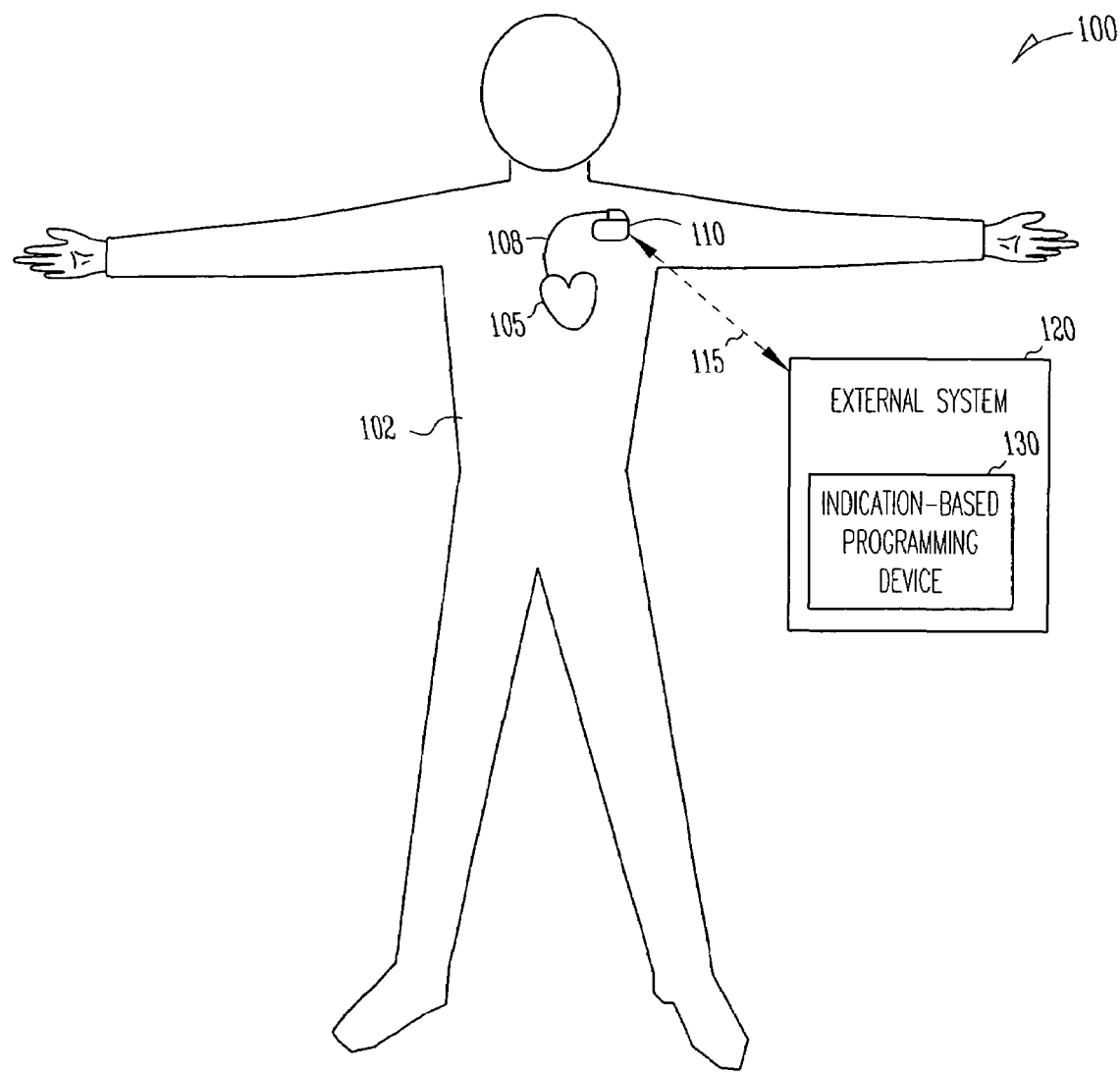
FIG. 1 is an illustration of an embodiment of a CRM system and portions of the environment in which the CRM system is used.

In the following detailed description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description provides examples, and the scope of the present invention is defined by the appended claims and their legal equivalents.

It should be noted that references to "an", "one", or "various" embodiments in this document are not necessarily to the same embodiment, and such references contemplate more than one embodiment.

In this document, an "indication" includes a symptom or particular circumstance that indicates the advisability or necessity of a specific medical treatment or procedure. An "indication for use of an implantable medical device" or "device indication" includes a symptom or particular circumstance that indicates the advisability or necessity of one or more specific medical treatments that are deliverable by an implantable medical device or one or more specific medical procedures that are performable by the implantable medical device.

This document discusses an indication-based programming method and programming device for an implantable medical device. The programming device collects patient-specific information including a patient's indications for use of the implantable medical device and automatically produces values for operational parameters enabling the implantable medical device to deliver one or more therapies according to the indications. In addition to the indications, the patient-specific information includes, but is not limited to, the patient's demographic data, cardiac history, electrogram, electrocardiogram (ECG), echocardiogram (indicative of ejection fraction, for example), physical attributes, non-cardiac disease history, and/or drug regimens. Further examples of such patient-specific information and an example of a system for determining patient-specific parameters for programming an implantable medical device are discussed in U.S. patent application Ser. No. 10/950,876, entitled "SYSTEM AND METHOD FOR DETERMINING PATIENT-SPECIFIC IMPLANTABLE MEDICAL DEVICE PROGRAMMING PARAMETERS," filed on Sep. 27, 2004, assigned to Cardiac Pacemakers, Inc., which is incorporated herein by reference in its entirety. The patient-specific information allows for optimization of therapy delivery for each individual patient. The values for the operational parameters produced by the programming device are then used to program the implantable medical device via telemetry. Thus, the programming device substantially automates the process between the diagnosis of the patient's indications and other conditions and the programming of the implantable medical device. The indication-based programming allows a user, such as a physician or other caregiver, to optimally utilize features and capabilities of an implantable medical device based on the patient's specific conditions.

FIG. 1 is an illustration of an embodiment of a CRM system 100 and portions of the environment in which CRM system 100 is used. System 100 includes an implantable medical device 110, a lead system 108, an external system 120, and a wireless telemetry link 115.

After implantation, implantable medical device 110 operates within a body 102 to sense activities of a heart 105 and deliver one or more therapies to heart 105. Implantable medical device 110 includes, but is not limited to, one or more of a pacemaker, a cardioverter/defibrillator, a cardiac resynchronization therapy (CRT) device, a cardiac remodeling control therapy (RCT) device, a drug delivery device, and a biological therapy device. A device type, such as a model number or a code that identifies the type of implantable medical device 110, indicates one or more available operational modes and a plurality of programmable parameters of implantable medical device 110. Each operational mode provides for one type of therapy deliverable by implantable medical device 110. In one embodiment, implantable medical device 110 is an implantable cardioverter/defibrillator with pacing capabilities and providing for operational modes including a bradycardia pacing mode, a CRT pacing mode, an RCT pacing mode, an anti-tachycardia pacing mode, and a defibrillation mode. Some or all of such operational modes are further differentiated into specific operational modes. For example, the bradycardia pacing mode includes standard pacing modes known in the art, such as the AOO, VOO, AAI, VVI, VVT, DVI, DDI, VDD, and DDD pacing modes and the rate-adaptive versions of these pacing modes. Each operational mode is associated with a plurality of operational parameters. Values for a set of operational parameters are programmed into implantable medical device 110 for it to operate in one or more operational modes selected according to a patient's conditions and therapeutic needs.

Lead system 108 provides one or more electrical and/or other connections between implantable medical device 110 and heart 105. In one embodiment, lead system 108 includes one or more pacing and/or defibrillation leads each having one or more electrodes for electrogram sensing and/or delivery of electrical pulses including pacing pulses and/or cardioversion/defibrillation pulses to heart 105. In one embodiment, one or more intracardiac sensors are incorporated into lead system 108 to sense signals such as heart sounds, intracardiac pressures, and chemical parameters of the blood.

External system 120 communicates with implantable medical device 110 through telemetry link 115. It allows the user and/or the patient to communicate with implantable medical device 110. External system 120 includes an indication-based programming device 130 that performs indication-based programming of implantable medical device 110. In addition to an indication-based programming mode, external system 120 also provides for a parameter-based programming mode. When operating in the indication-based programming mode, indication-based programming device 130 collects patient-specific information and produces the values for the set of operational parameters for programming implantable medical device 110 to operate in one or more of its available operational modes based on the patient-specific information. When operating in the parameter-based programming mode, external system 120 presents parameters used in its one or more current operational modes with their current values and allows the user to adjust the current values. In one embodiment, in addition to the indication-based programming mode and the parameter-based programming mode, external system 120 further provides for a question-based programming mode. When operating in the question-based programming mode, external system 120 asks the user a sequence of questions. Based on at least the answers to these questions, external system 120 determines the values for the set of operational parameters for programming implantable medical device 110 to operate in one or more of its operational modes. An example of the question-based programming is discussed in U.S. patent application Ser. No. 10/844,642, "METHOD AND APPARATUS FOR QUESTION-BASED PROGRAMMING OF CARDIAC RHYTHM MANAGEMENT DEVICES," filed on May 13, 2004, assigned to Cardiac Pacemakers, Inc., which is incorporated herein by reference in its entirety.

For illustrative purposes, specific embodiments of external system 120 are discussed below with reference to FIGS. 2-4. In a specific embodiment, external system 120 includes portions of a system for determining patient-specific implantable medical device programming parameters that is discussed in U.S. patent application Ser. No. 10/950,876.

Telemetry link 115 provides for data transmissions between implantable medical device 110 and external system 120. In one embodiment, telemetry link 115 is an inductive (magnetic) telemetry link. In another embodiment, telemetry link 115 is a far-field radio-frequency electromagnetic telemetry link. In various other embodiments, telemetry link 115 uses other types of media suitable for wireless data transmissions between an implantable medical device and an external system 120, such as ultrasound. Telemetry link 115 provides for data transmission from implantable medical device 110 to external system 120. This includes, for example, transmitting information indicative of the device type of implantable medical device 110, transmitting data indicative of the current operational mode(s) and parameter values, transmitting real-time physiological data acquired by implantable medical device 110, extracting physiological data acquired by and stored in implantable medical device 110, extracting therapy history data, and/or extracting data indicating an operational status (e.g., battery status and lead impedance). The physiological data represent signals acquired by implantable medical device 110 using one or more sensors included in, and/or connected to, implantable medical device 110. In one embodiment, one or more such sensors are incorporated into lead system 108. The signals include, but not being limited to, one or more of electrograms, heart sounds or a signal indicative of heart sounds, activity level signal, impedance signal, pressure or pressure-indicating signal, and respiratory signal. In one embodiment, the physiological data also include parameters measured from one or more of these signals. In one embodiment, external system 120 or the user determines parameter values for programming implantable medical device 110 based on these physiological data. Telemetry link 115 also provides for data transmission from external system 120 to implantable medical device 110. This includes, for example, parameters for programming implantable medical device 110 to operate in one or more of its available operational modes and to perform at least one self-diagnostic test (such as for a battery status or a lead impedance value).

Figure 2:
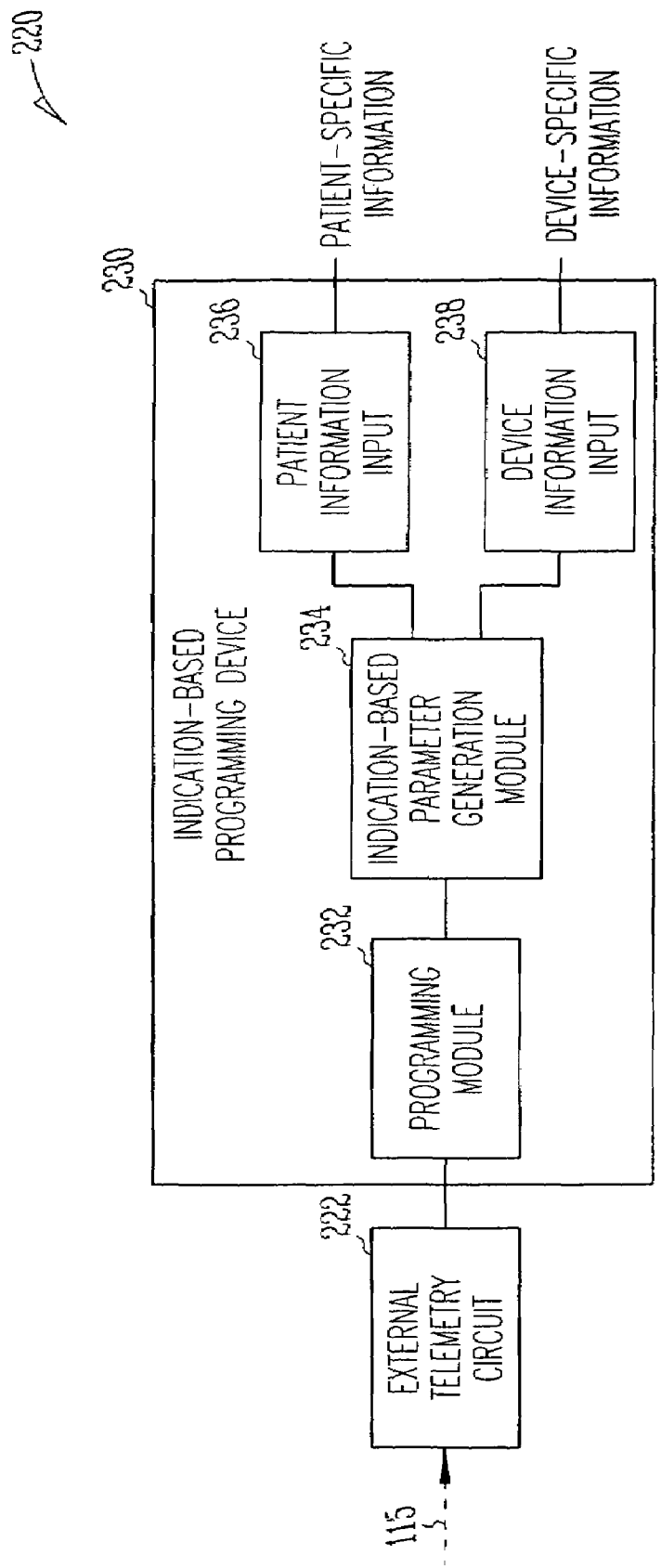
FIG. 2 is a block diagram illustrating an embodiment of portions of the circuit of an external system performing indication-based programming of an implantable medical device.

FIG. 2 is a block diagram illustrating an embodiment of portions of the circuit of an external system 220, which is a specific embodiment of external system 120. External system 220 includes an external telemetry circuit 222 and an indication-based programming device 230. External telemetry circuit 222 communicates with implantable medical device 110 via telemetry link 115.

Indication-based programming device 230 is a specific embodiment of indication-based programming device 130 and includes a patient information input 236, a device information input 238, an indication-based parameter generation module 234, and a programming module 232. Patient information input 236 receives patient-specific information including indications for use of the implantable medical device. In various embodiments, patient information input 236 receives patient-specific information from one or more of implantable medical device 110, another one or more implantable devices implanted in the patient, sensors externally attached to the patient, a physician or other caregiver through a user interface of external system 220, electronic medical records of the patient stored in one or more locations in external system 220, and any relevant records made available to external system 220. Device information input 238 receives device-specific information including a device type indicative of a plurality of programmable parameters. In various embodiments, device information input 238 receives device-specific information from implantable medical device 110 and/or one or more locations in external system 220. Indication-based parameter generation module 234 produces values for a set of operational parameters of the plurality of programmable parameters based on the patient-specific information and the device-specific information. Programming module 232 programs the implantable medical device by converting the values for the set of operational parameters into a programming code and causing external telemetry circuit 222 to transmit the programming code to implantable medical device 110 via telemetry link 115.

Figure 3:
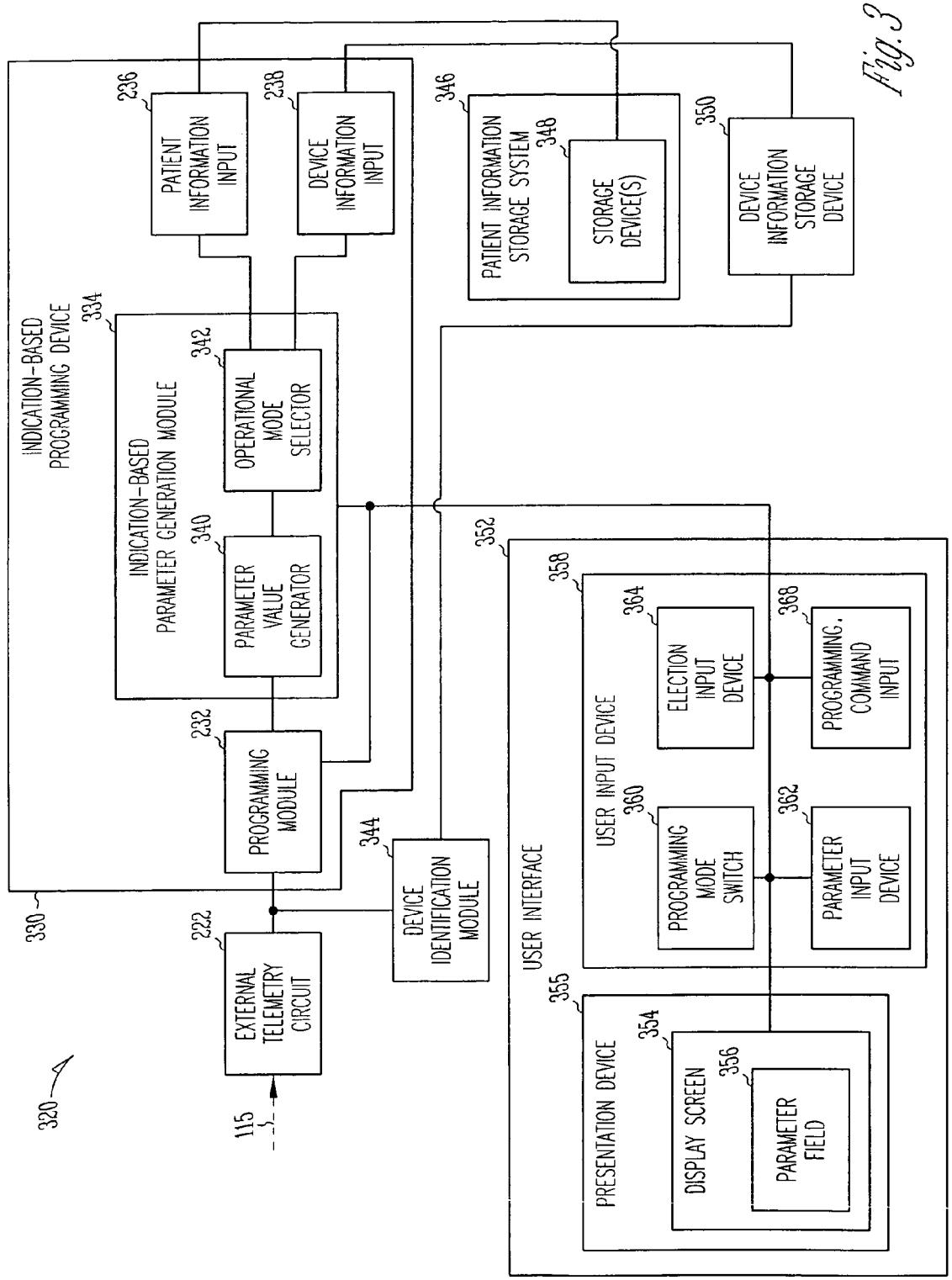
FIG. 3 is a block diagram illustrating a specific embodiment of portions of the circuit of the external system.

FIG. 3 is a block diagram illustrating an embodiment of portions of the circuit of an external system 320, which is a specific embodiment of external system 220. External system 320 includes external telemetry circuit 222, an indication-based programming device 330, a device identification module 344, a patient information storage system 346, a device information storage device 350, and a user interface 352.

Indication-based programming device 330 is a specific embodiment of indication-based programming device 230 and includes patient information input 236, device information input 238, an indication-based parameter generation module 334, and programming module 232. Indication-based parameter generation module 334 is a specific embodiment of indication-based parameter generation module 234 and produces values for the set of operational parameters based on the patient-specific information and the device-specific information. The set of operational parameters enables the implantable medical device to operate in at least one of its available operational modes. In one embodiment, as illustrated in FIG. 3, indication-based parameter generation module 334 includes an operational mode selector 342 and a parameter value generator 340. Operational mode selector 342 selects at least one operational mode from the available operational modes of implantable medical device 110. In one embodiment, operational mode selector 342 selects the operational mode(s) based on the patient-specific information and the device-specific information. In another embodiment, operational mode selector 342 selects the operational mode(s) based on a user selection and includes a mode input to receive the user selection. Parameter value generator 340 produces the values of the set of operational parameters enabling implantable medical device 110 to operate in the selected operational mode(s) based on the patient-specific information and the device-specific information. In another embodiment, indication-based parameter generation module 334 includes an indication-based programming algorithm execution module such as a mapping algorithm execution module to execute a mapping algorithm relating the patient-specific information to the device-specific information.

Device identification module 344 identifies the device type of implantable medical device 110 based on information received by external telemetry circuit 222 from implantable medical device 110. The device type indicates the available operational modes and the programmable parameters of implantable medical device 110. In one embodiment, device identification module 344 includes a device model identification module to identify a model number indicative of the device type. In another embodiment, device identification module 344 includes a device code identification module to identify a device code indicative of the device type.

Patient information storage system 346 includes one or more storage devices 348 to store patient-specific information including, but not being limited to, some or all of indications for use of the implantable medical device, demographic data, cardiac history, electrogram, ECG, physical attributes, non-cardiac disease history, and drug regimens. In one embodiment, the patient-specific information is stored as electronic medical records. In one embodiment, the patient-specific information includes information acquired by an outpatient system performing continuous monitoring, diagnostic, and patient management functions including continuous ECG monitoring and analysis. Such a system allows continuous signal acquisition and/or analysis for a relatively long period of time, such as 24 hours or longer. One example of such a system includes a Holter monitor, which is known in the art as a portable device worn by a patient during the course of daily activities for continuously recording cardiac electrical activity of the patient. Another example of such a system is an outpatient mobile telemetry system providing for ECG monitoring and analysis used by CardioNet (San Diego, Calif.) to provide monitoring and patient management services.

Device information storage device 350 stores the device-specific information. In one embodiment, device information storage device 350 stores device information data sets each specific to one type of implantable medical devices programmable by external system 320. The stored device-specific information is updated when additional information is made available, such as when a new way of using an existing implantable medical device is developed. In one embodiment, when external system 320 receives additional and/or modified device information data for an existing type implantable medical device, the device information data set stored in device information storage device 350 for that existing type implantable medical device is updated accordingly.

In one embodiment, upon establishment of telemetry link 115, device identification module 344 identifies the device type of implantable medical device 110, and the device-specific information is extracted from device information storage device 350 according to the identified device type. Device information input 238 then receives the extracted device-specific information.

User interface device 352 includes a presentation device 355 and a user input device 358. Presentation device 355 includes a display screen 354. Display screen 354 includes a parameter field 356 to display the values for the set of operational parameters. In one embodiment, presentation device 355 further includes a printer to print information including the values for the set of operational parameters. User input device 358 includes a programming mode switch 360, an election input device 364, a parameter input device 362, and a programming command input 368. Programming mode switch 360 allows the user to select the indication-based programming mode or the parameter-based programming mode. In one embodiment, programming mode switch 360 allows the user to switch between the indication-based programming mode and the parameter-based programming mode during a programming process. Election input device 364 allows the user to accept, modify, or discard the values for the set of operational parameters. Parameter input device 362 allows the user to modify one or more of the values for the set of operational parameters if the user has elected to modify the values. Programming command input 368 allows the user to enter a command for programming the implantable medical device using the values for the set of operational parameters. In one embodiment, display screen 354 is an interactive screen that is part of user input device 358. Programming mode switch 360 includes a programming mode change button displayed on the interactive screen. Election input device 364 includes election buttons displayed on the interactive screen. Parameter field 356 is an interactive parameter field being part of parameter input device 362. The interactive parameter field allows modification of the displayed values for the set of operational parameters. Programming command input 368 includes a programming mode change button displayed on the interactive screen. In another embodiment, one or more of programming mode switch 360, election input device 364, parameter input device 362, and programming command input 368 includes part of display screen 354, which is an interactive screen, while the remaining input device(s) include switches, keys, knobs, and/or other mechanical devices. In another embodiment, programming mode switch 360, election input device 364, parameter input device 362, and programming command input 368 each include one or more switches, keys, knobs, and/or other mechanical devices.

Figure 4:
FIG. 4 is a block diagram illustrating an embodiment of the external system.

FIG. 4 is a block diagram illustrating an embodiment of external system 420. External system 420 is a specific embodiment of external system 120 and, in one embodiment, represents an exemplary structural arrangement for external system 220 or 320. As illustrated in FIG. 4, external system 420 is a patient management system including an external device 370, a telecommunication network 372, and one or more remote devices 374. External device 370 is placed within the vicinity of implantable medical device 110 and communicates with implantable medical device 110 via telemetry link 115. Remote device(s) 374 are in one or more remote locations and communicates with external device 370 through telecommunication network 372, thus allowing the user to monitor and treat the patient from a distant location and/or allowing collection of patient information from the one or more remote locations. In one specific embodiment, external device 370 includes indication-based programming device 130 (including any of its specific embodiment). In another specific embodiment, remote device(s) 374 include indication-based programming device 130 (including any of its specific embodiment). In another embodiment, indication-based programming device 130 (including any of its specific embodiments) is distributed in both external device 370 and remote device(s) 374.

Telecommunication network 372 allows for communication between an operation room, an electrophysiology laboratory, or other facility where implantable medical device 110 is programmed and one or more remote data storage facilities where the patient-specific information is located. In one embodiment, external system 420 is used during an implantation operation. External device 370 is placed in or near an operation room where implantable medical device 110 is implanted into a patient. Remote device(s) 374 include a data base containing the patient's electronic medical records. Communication between external device 370 and the data base is established to allow indication-based programming device 130 to collect patient-specific information from the patient's electronic medical records. Indication-based programming device 130 then generates a programming code including parameter values required for implantable medical device 110 to deliver one or more therapies approximately optimized based on the patient-specific information. Thus, external system 420 provides for a substantially automated process for programming implantable medical device 110 during the implantation operation.

Figure 5:
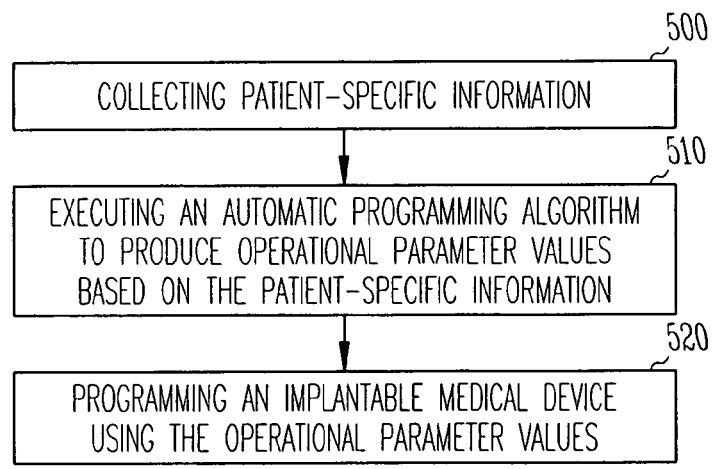
FIG. 5 is a flow chart illustrating an embodiment of a method for indication-based programming of an implantable medical device.

FIG. 5 is a flow chart illustrating an embodiment of a method for an indication-based programming of an implantable medical device. The method substantially automates the process between the diagnosis of a patient and the programming of the implantable medical device if the patient is indicated for a device therapy as the result of the diagnosis. In one embodiment, the method is performed with external system 220.

Patient-specific information is collected at 500. The patient-specific information includes indications for use of the implantable medical device. An indication-based automatic programming algorithm is executed at 510 to produce values for a set of operational parameters based on the patient-specific information. The set of operational parameters enables the implantable medical device to deliver one or more therapies treating the patient's indications. The implantable medical device is programmed using the values for the set of operational parameters at 520. In one embodiment, the implantable device is automatically programmed after the values for the set of operational parameters are produced. In another embodiment, after the values for the set of operational parameters are produced, the user reviews the values, modifies the values when appropriate or necessary, and the implantable medical device is then programmed.

Figure 6:
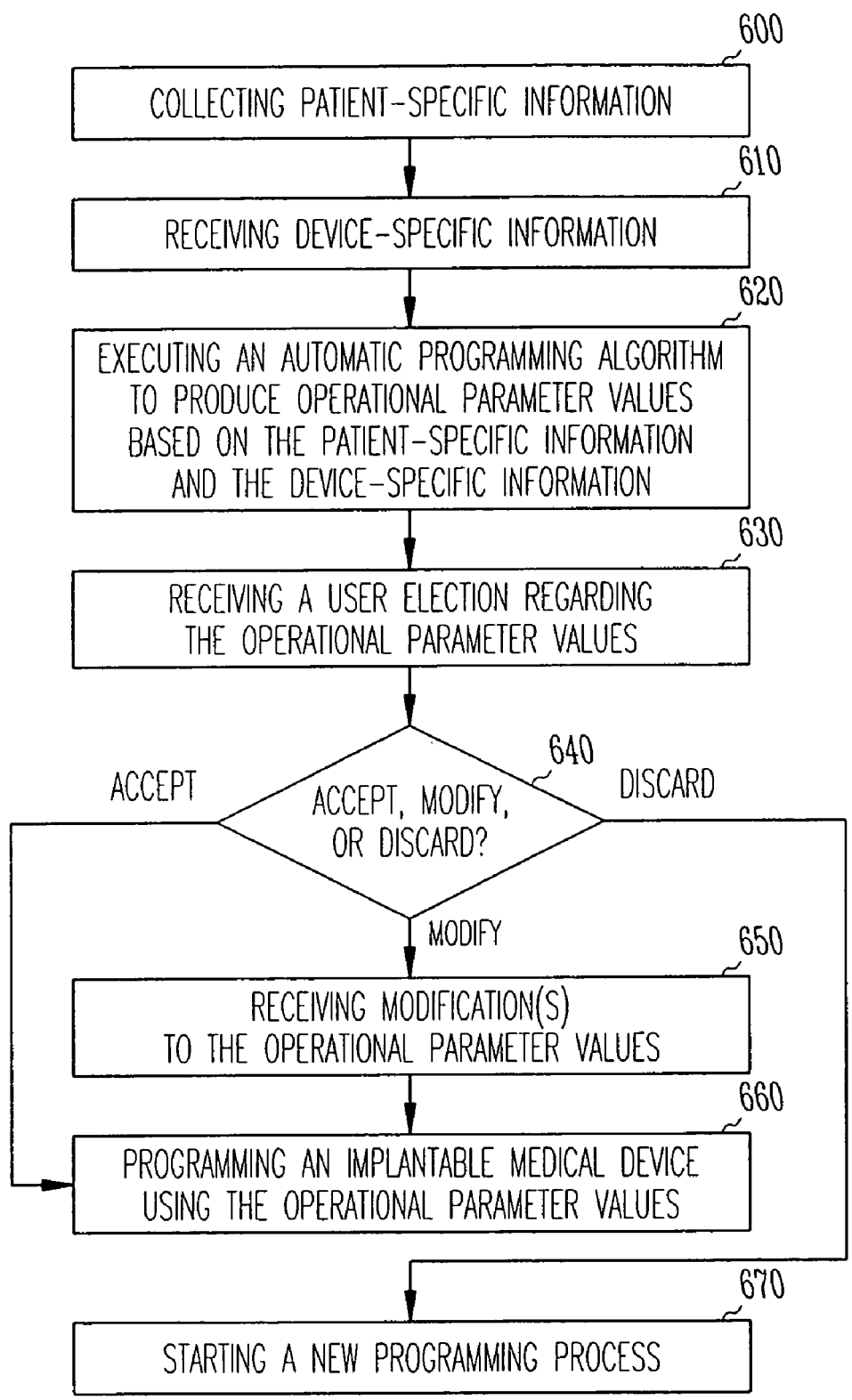
FIG. 6 is a flow chart illustrating a specific embodiment of the method for indication-based programming of the implantable medical device.

FIG. 6 is a flow chart illustrating a specific embodiment of the method for the indication-based programming of the implantable medical device. In one embodiment, the method is performed with external system 320. The implantable medical device includes, but is not limited to, a pacemaker, a cardioverter/defibrillator, a CRT device, and an RCT device.

Patient-specific information is collected at 600. In one embodiment, the patient-specific information includes indications for use of the implantable medical device. In a further embodiment, in addition to the indications for use of the implantable medical device, the patient-specific information includes one or more of demographic data, cardiac history, electrogram, ECG, echocardiogram, physical attributes, non-cardiac disease history, and drug regimens. In one embodiment, collecting the patient-specific information includes extracting information from an electronic medical record. In one embodiment, collecting the patient-specific information includes extracting information from results of one or more electrophysiological tests. In one embodiment, collecting the patient-specific information includes extracting information from the implantable medical device.

Device-specific information is received at 610. The device-specific information includes a device type of the implantable medical device. The device type indicates the available operational modes and the programmable parameters of the implantable medical device. Each operational mode is supported by a set of operational parameters including one or more of the programmable parameters.

An indication-based programming algorithm is executed at 620 to produce values for the set of operational parameters based on the patient-specific information and the device-specific information. In one embodiment, the indication-based programming algorithm automatically selects one or more operational modes from the available operational modes of the implantable medical device based on the patient-specific information and the device-specific information. The values for the set of operational parameters are then produced to enable the implantable medical device to operate in the automatically selected operational mode(s). In another embodiment, the user selects one or more operational modes from the available operational modes of the implantable medical device based on the patient-specific information, the device-specific information, and professional judgment. The values for the set of operational parameters are then produced to enable the implantable medical device to operate in the user-selected operational mode(s). In one embodiment, the indication-based programming algorithm is a mapping algorithm relating the patient-specific information to the device-specific information of the implantable medical device. The mapping algorithm selects one or more operational modes from the available operational modes of the implantable medical device and/or produces the values for the set of operational parameters enabling the implantable medical device to operate in the selected operational mode(s).

A user election regarding the handling of the values for the set of operational parameters is received at 630. In one embodiment, the values for the set of operational parameters are presented to the user for review. The user is then asked to elect to accept, modify, or discard the values for the set of operational parameters. If an election to accept the values for the set of operational parameters is received at 640, the implantable medical device is programmed using the values for the set of operational parameters at 660. If an election to modify the values for the set of operational parameters is received at 640, one or more modified values for the set of operational parameters are received at 650. In one embodiment, the received one or more modified values are checked against one or more predetermined safety limits. If any modified value for an operational parameter exceeds the predetermined safety limit for that parameter, the user is asked to reenter the value for that parameter. In another embodiment, the one or more modified values are entered by selecting values and/or value ranges presented to the user. The presented values and/or value ranges are within the predetermined safety limits. Then, the implantable medical device is programmed using the one or more modified values for the set of operational parameters at 660. If an election to discard the values for the set of operational parameters is received at 640, a new programming process is started at 670. The user may, for example, choose to repeat the steps starting at 600 after making additional and/or alternative patient-specific information available for collection. The user may also choose to switch to the parameter-based programming mode or the question-based programming mode.

In one exemplary application of the indication-based programming, a patient's electronic medical record is reviewed to determine whether the patient is indicated for use of an implantable cardioverter/defibrillator (ICD) based on criteria developed from results of a clinical study with a patient population. Examples of such a clinical study are discussed in Prystowsky, "A Guide to Device Selection: Cardiac Resynchronization Therapy Alone or in Combination with an Implantable Cardioverter Defibrillator," *Rev. Cardiovasc. Med.*, 2003; 4 (Suppl 2): S47-S54). The ICD is capable of delivering pacing and cardioversion/defibrillation therapies. If the patient is indicated for both ventricular defibrillation therapy and anti-tachycardia pacing (ATP) therapy, data from an electrophysiology test and Holter recordings are analyzed. The analysis results in, among other things, a threshold heart rate above which the ventricular defibrillation therapy is to be immediately delivered and another threshold heart rate above which an ATP therapy is to be delivered. The analysis may also result in information related to the morphological features of an electrogram associated with a known cardiac rhythm for purposes of discrimination between various types of arrhythmia. The discrimination leads to classification of a tachyarrhythmia, and an appropriate therapy is delivered according to the classification. If the electronic medical records further indicate that the patient has a family history of syncope, a monitoring zone is set at lower heart rates to capture episodes of slow ventricular tachycardia in order to determine whether the syncope is cardiac mediated.

It is to be understood that the above detailed description is intended to be illustrative, and not restrictive. For example, while a CRM system is specifically discussed in the description above, the present subject matter is generally applicable to various types of medical device systems. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An external system for programming an implantable medical device, the system comprising:
    an external telemetry circuit configured to communicate with the implantable medical device; and
    an indication-based programming device including:
        a patient information input to receive patient-specific information including indications for use of the implantable medical device;
        a device information input to receive device-specific information including a device type indicative of a plurality of programmable parameters;
        an indication-based parameter generation module coupled to the patient information input and the device information input, the indication-based parameter generation module adapted to produce values for a set of operational parameters of the plurality of programmable parameters based on the patient-specific information and the device-specific information; and
        a programming module coupled to the external telemetry circuit and the indication-based parameter generation module, the programming module adapted to program the implantable medical device using the values of the set of operational parameters.

2. The system of claim 1, wherein the indication-based parameter generation module comprises:
    an operational mode selector to select at least one operational mode from a plurality of available operational modes of the implantable medical device based on the patient-specific information and the device-specific information; and
    a parameter value generator to produce the values of the set of operational parameters being values of parameters enabling the implantable medical device to operate in the selected at least one operational mode.

3. The system of claim 1, wherein the indication-based parameter generation module comprises:
    an operational mode selector to select at least one operational mode from a plurality of available operational modes of the implantable medical device based on a user selection, the operational mode selector including a mode input to receive the user selection; and
    a parameter value generator to produce the values of the set of operational parameters being values of parameters enabling the implantable medical device to operate in the selected at least one operational mode.

4. The system of claim 1, wherein the indication-based parameter generation module comprises a mapping algorithm execution module adapted to execute a mapping algorithm relating the patient-specific information to the device-specific information.

5. The system of claim 1, further comprising a user interface device coupled to the indication-based programming device, the user interface device including:
    a display screen including a parameter field to display the values for the set of operational parameters; and
    an election input device to receive a user election to accept, modify, or discard the values of the set of operational parameters.

6. The system of claim 5, wherein the election input device comprises election buttons displayed on the display screen.

7. The system of claim 5, wherein the user interface device further comprises a parameter input device allowing modification of the values for the set of operational parameters.

8. The system of claim 7, wherein the display screen is an interactive screen, the parameter field is adapted to allow modification of the displayed values for the set of operational parameters, and the parameter input device comprises portions of the parameter field.

9. The system of claim 5, wherein the user interface further comprises a user-controllable programming mode switch configured for selecting one of an indication-based programming mode and a parameter-based programming mode and for switching between the indication-based programming mode and the parameter-based programming mode.

10. The system of claim 1, further comprising a patient information storage system coupled to the patient information input, the patient information storage system including one or more storage devices configured to store the patient-specific information.

11. The system of claim 10, wherein the one or more storage devices are each configured to store one or more of the indications for use of the implantable medical device, demographic data, cardiac history, electrogram, electrocardiogram, echocardiogram, physical attributes, non-cardiac disease history, and drug regimens.

12. The system of claim 10, further comprising a telecommunication network, and wherein at least one of the one or more storage devices are coupled to the patient information input via the telecommunication network.

13. The system of claim 12, further comprising a device information storage device to store the device-specific information for a plurality of device types.

14. The system of claim 13, further comprising a device identification module to identify the device type of the implantable medical device based on information received by the external telemetry circuit from the implantable medical device.

15. A cardiac rhythm management (CRM) system, comprising:
   an implantable medical device of a type identified by a device type indicative of one or more available operational modes and a plurality of programmable parameters; and
   an external system including:
      an external telemetry circuit configured to communicate with the implantable medical device; and
      an indication-based programming device including:
         a patient information input to receive patient-specific information including indications for use of the implantable medical device;
         a device information input to receive device-specific information including the device type;
         an indication-based parameter generation module coupled to the patient information input and the device information input, the indication-based parameter generation module adapted to produce values for a set of operational parameters of the plurality of programmable parameters based on the patient-specific information and the device-specific information, the values for the set of operational parameters enabling the implantable medical device to operation in at one of the one or more operational modes; and
         a programming module coupled to the indication-based parameter generation module and the external telemetry circuit, the programming module adapted to program the implantable medical device using the values of the set of operational parameters.

16. The CRM system of claim 15, further comprising a user interface device configured to allow modification of the values of the set of operational parameters before the programming module programs the implantable medical device using the values of the set of operational parameters.

17. The CRM system of claim 15, wherein the external system comprises a patient management system including:
   an external device communicatively coupled to the implantable medical device via telemetry;
   a telecommunication network coupled to the external device; and
   one or more remote devices coupled to the telecommunication network.

18. The CRM system of claim 17, wherein the one or more remote devices comprises at least one storage device configured to store portions of the patient-specific information.

19. The CRM system of claim 18, wherein the external system further comprises a device identification module to identify the device type of the implantable medical device based on information received from the implantable medical device via the telemetry link.

20. The CRM system of claim 15, wherein the implantable medical device comprises one or more of a pacemaker and a cardioverter/defibrillator.

21. The CRM system of claim 15, wherein the implantable medical device comprises one or more of a cardiac resynchronization device and a cardiac remodeling device.

22. A method for programming an implantable medical device, the method comprising:
   collecting patient-specific information including indications for use of the implantable medical device;
   receiving device-specific information including a device type of the implantable medical device, the device type indicative of one or more available operational modes and a plurality of programmable parameters;
   executing an indication-based programming algorithm to produce values for a set of operational parameters of the plurality of programmable parameters based on the patient-specific information and the device-specific information; and
   receiving a user election to accept, modify, or discard the values for the set of operational parameters.

23. The method of claim 22, wherein executing the indication-based programming algorithm comprises:
   selecting at least one operational mode from the one or more available operational modes; and
   producing the values for the set of operational parameters being values of parameters enabling the implantable medical device to operate in the selected at least one operational mode.

24. The method of claim 22, wherein executing the indication-based programming algorithm comprises:
   receiving a user selection of at least one operational mode of the one or more available operational modes; and
   producing the values for the set of operational parameters being values of parameters enabling the implantable medical device to operate in the user-selected at least one operational mode.

25. The method of claim 22, wherein executing the indication-based programming algorithm comprises executing a mapping algorithm relating the patient-specific information to the device-specific information of the implantable medical device.

26. The method of claim 22, further comprising programming the implantable medical device using the values for the set of operational parameters if a user election to accept the values for the set of operational parameters is received.

27. The method of claim 26, further comprising:
receiving one or more modified values for the set of operational parameters if a user election to modify the set of operational parameters is received; and
programming the implantable medical device using the one or more modified values for the set of operational parameters.

28. The method of claim 27, further comprising checking the one or more modified values for the set of operational parameters against one or more predetermined safety limits before programming the implantable medical device using the one or more modified values for the set of operational parameters.

29. The method of claim 27, wherein programming the implantable medical device comprises programming an implantable pacemaker.

30. The method of claim 27, wherein programming the implantable medical device comprises programming an implantable cardioverter/defibrillator.

31. The method of claim 27, wherein programming the implantable medical device comprises programming an implantable cardiac resynchronization therapy device.

32. The method of claim 27, wherein programming the implantable medical device comprises programming an implantable cardiac remodeling control therapy device.

33. The method of claim 22, wherein collecting patient-specific information comprises collecting one or more of the indications for use of the implantable medical device, demographic data, cardiac history, electrogram, electrocardiogram, echocardiogram, physical attributes, non-cardiac disease history, and drug regimens.

34. The method of claim 33, wherein collecting patient-specific information comprises extracting information from an electronic medical record.

35. The method of claim 33, wherein collecting patient-specific information comprises extracting information from results of one or more electrophysiology tests.

36. The method of claim 33, wherein collecting patient-specific information comprises receiving at least a portion of the patient-specific information from a remote location via a telecommunication network.

* * * * *